United States Patent [19]
Dong et al.

[11] Patent Number: 5,220,043
[45] Date of Patent: Jun. 15, 1993

[54] SYNTHESIS OF D-ERYTHRO-SPHINGOMYELINS

[75] Inventors: Zhengxin Dong, Brighton, Mass.; Jared A. Butcher, Jr., Athens, Ohio

[73] Assignee: Ohio University, Athens, Ohio

[21] Appl. No.: 672,944

[22] Filed: Mar. 21, 1991

[51] Int. Cl.$^5$ .............................................. C07F 9/02
[52] U.S. Cl. ...................................... 554/82; 554/78; 554/79; 554/80
[58] Field of Search ...................... 554/80, 82, 78, 79; 568/305, 307

[56] References Cited

FOREIGN PATENT DOCUMENTS 2-101009 4/1990 Japan .

OTHER PUBLICATIONS

Evankooa et al, Chemical Abstracts, vol. 82, #15, pp. 405-406, 1975, 97613f.
Shapiro et al, "Studies of Sphingolipids, VII, Synthesis and Configuration of Natural Sphingomyelins", *Journal of the American Chemical Society*, vol. 84, pp. 1047-1050, Mar. 20, 1962.
Bruzik, "The Synthesis and Absolute Configuration of This Thiosphingomyelins", *Journal of the Chemical Society, Chemical Communication*, pp. 329-331, (1986).
Zimmermann et al, "Synthesis von erythro-Sphingosinen über die Azidoderivate", *Liebigs Ann. Chem.*, pp. 663-667, (1988).
Nicolaou et al, "A Practical and Enantioselective Synthesis of Glycosphingolipds and Related Compounds. Total Synthesis of Globotriaosylceramide (GB$_3$)", *J. Amer. Chem. Soc.*, vol. 110, No. 23, pp. 7910-7912, (1988).
Uzomba, "Syntheses of Labeled Fatty Acids and Dipalmitoyl-Sn-Glycerol-3-Phosphatidylcholine: Dynamic and Order Study of the Acyl Chain Using $^{13}$C Spin--Lattice Relaxation Measurements", Ph.D. Dissertation, Ohio University, *Diss. Abstr. Int. B.*, 49(a), 3771-2, (1989).
Sripada et al, "Partial synthesis and properties of a series of N-acyl sphingomyelins", *Journal of Lipid Research*, vol. 28, pp. 710-718, (1987).
Edmundson, "Oxidation of Cyclic Phosphorochloridites", *Chemistry and Industry*, pp. 1828-1829, Oct. 20, 1962.
Lucas et al, "Cyclic Phosphites of Some Aliphatic Glycols", vol. 72, pp. 5491-5497, Dec. 1950.
Thuong et al, "Nouvelle methodé de préparation de la phosphorylcholine, de la phosphorylhomocholine et de leurs dérivés", *Bulletin de la Societe Chimique de France*, No. 3-4, pp. 667-671, 1974.
Tkaczuk et al, "Useful Syntheses of erythro- and threo-N-oleoyl-D-sphingosines (Ceramides) and Galactosylceramides (Cerebrosides) from L-Serine", *J. Org. Chem.*, vol. 46, No. 22, pp. 4393-4398, 1981.
Mungall et al, "Use of the Azido Group in the Synthesis of 5'Terminal Aminodeoxythymide Oligonucleotides", *J. Org. Chem.*, vol. 40, No. 11, pp. 1659-1662, 1975.
Belleau et al, "A New Convenient Reagent for Peptide Synthesis", *Journal of the American Chemical Society*, 90:6, pp. 1651-1652, Mar. 13, 1968.
Höfle et al, "4-Dialkylaminopyridines as Highly Active Acylation Catalysts", *Angew. Chem. Int. Ed. Engl.*, 17, pp. 569-583, 1978.
Chandrakumar et al, "Stereospecific Synthesis of Ether Phospholipids. Preparation of 1-Alkyl-2-(acylamino)-2-deoxyglycerophosphorylcholines", *J. Org. Chem.*, vol. 48, No. 8, pp. 1197-1202, 1983.
Corey et al, "Protection of Hydroxyl Groups as tert-Butyldimethylsilyl Derivatives", *Journal of The American Chemical Society*, 94:17, pp. 6190-6191, Aug. 23, 1972.
Koike et al, "A Highly Stereoselective Synthesis of 2(S), 3(R), 4E- and 2(S), 3(R), 4Z-N-Tetracosanoylsphingenine from D-Glucose", *Carbohydrate Research*, 158, pp. 113-123, 1986.

*Primary Examiner*—José G. Dees
*Assistant Examiner*—Deborah D. Carr
*Attorney, Agent, or Firm*—Killworth, Gottman, Hagan & Schaeff

[57] ABSTRACT

A method for making optically pure D-erythro-sphingomyelins which may be labeled for identification and testing purposes is provided. The present method is directed to a five step synthesis comprising the steps of: (1) reacting a (2S,3R,4E)-2-azido-octadecen-1,3-diol composition having a protective functional group attached thereto with a solution of triphenylphosphine and water in a first solvent to form a protected sphingosine; (2) reacting a long-chain fatty acid with the protected sphingosine in the presence of N-ethoxycarbonyl-2-ethoxy-1,2-dihydroquinoline catalyst in a second solvent to form a protected ceramide; (3) reacting 2-chloro-2-oxo-1,3,2-dioxaphospholane with the protected ceramide in the presence of triethylamine and 4-dimethylaminopyridine catalyst in a third solvent to form a protected cyclic phosphotriester; (4) reacting trimethylamine with the protected cyclic phosphotriester in a solvent system to form a protected sphingomyelin; and (5) reacting tetra-n-butylammonium fluoride with the protected sphingomyelin in tetrahydrofuran to form the D-erythro-sphingomyelin composition.

20 Claims, No Drawings

SYNTHESIS OF D-ERYTHRO-SPHINGOMYELINS

BACKGROUND OF THE INVENTION

The present invention relates to a method for making sphingomyelins and to the product produced thereby. More particularly, the present invention relates to a method for making optically pure D-erythro-sphingomyelins which may be labeled for identification and testing purposes.

Sphingomyelin is a naturally occurring composition found in most biological plasma membranes. As is known, sphingomyelin (N-acyl sphingosine-1-phosphocholine or ceramide-1-phosphocholine) consists of three components, namely, sphingosine, a fatty acid and phosphorylcholine. The structure of naturally occurring sphingosine may be defined as trans-D-erythro-2-amino-4-octadecene-1,3-diol or (2S,3R,4E)-2-amino-4-octadecene-1,3-diol and has the structural formula

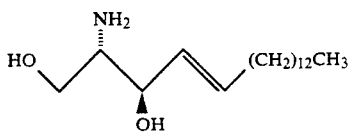

When the amino group of sphingosine is linked to a fatty acid, the formed compound is referred to as a ceramide and has the structural formula

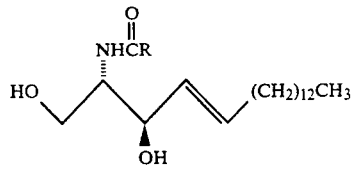

wherein R is an alkyl long-chain group of a fatty acid which typically has from fifteen to twenty-four carbon atoms. The third part of sphingomyelin is a phosphorylcholine group which is linked to the primary alcohol of ceramide. The phosphorylcholine group of sphingomyelin has the structural formula

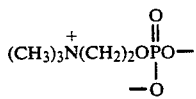

The phosphorylcholine is attached at the primary alcohol group as shown by the structural formula of sphingomyelin

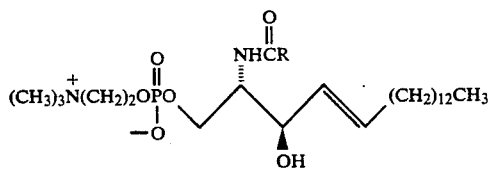

wherein R is an alkyl group of a long-chain fatty acid. Sphingomyelins which have a structural formula as illustrated are commonly found in biological plasma membranes of mammals.

As is well known, cells are characterized by a cytoplasmic membrane commonly referred to as a plasma membrane. This membrane creates a physical barrier by encapsulating the cytoplasm and providing internal compartments in which biological functions are carried out. This physical barrier created by the plasma membranes is necessary for the survival of the cell, such that the membrane excludes harmful substances, permits the acquisition of nutrients and energy and allows for the disposal of toxic materials from within the cell. In contrast to prokaryotic cells, eukaryotic cells include numerous intracellular organelles of widely different structures and functions, each bounded by its own membrane. Sphingomyelins are found in both plasma membranes and organelles of most mammalian tissues.

As is well known in the art, the essential structural unit of a biological membrane is the lipid molecule found in a bilayer arrangement. Within a biological membrane, these lipid molecules are interspersed with proteins which partially or completely traverse the bilayer via hydrophobic interactions, thus producing a mosaic of proteins and lipids. It has been shown that the most common lipids found in biological membranes are phospholipids. Particularly, phospholipids are essential for biological plasma membranes commonly found in the nervous tissue of all animal species. Sphingomyelin is one of those phospholipids.

Sphingomyelins have a high commercial value, especially in scientific research, medical studies, diagnostic testing and in the cosmetic industry. Some scientific research is focused on the regulation of sphingomyelin metabolism in biological systems. Many research laboratories study the influence of lipids on the activity of biological membranes and biological membrane-bound proteins. Much of this work is directed toward studying the dynamics of drug delivery, especially across the membranes of blood and nervous systems. Sphingomyelins have also gained great attention in brain and aging studies. Furthermore, several diseases, such as Niemann-Pick, atherosclerosis, cancer and some genetically transmitted diseases have been associated with abnormalities in sphingomyelin metabolism.

Thus, isolating and identifying sphingomyelins would be extremely beneficial when conducting medical studies and diagnostic testing relating to these diseases. However, naturally occurring sphingomyelins are heterogeneous in that they contain a multitude of sphingomyelins each having a variety of fatty acid chains attached thereto. Furthermore, naturally occurring sphingomyelins also contain small amounts of differing backbone long-chain bases, such as dihydrosphingosine and 4-hydroxyshinganine. Because of the heterogeneous character of naturally occurring sphingomyelins, it is extremely difficult to successfully conduct the desired scientific studies which require optically pure homogeneous sphingomyelins. Accordingly, it would be extremely desirable to have a method for producing homogeneous sphingomyelins that are optically pure. The most desirable sphingomyelins for these purposes may be referred to as D-erythro-sphingomyelins.

In addition to those qualities, it would also be desirable to have D-erythro-sphingomyelins having the ability of being labeled. Such labeled D-erythro-sphingomyelins are most suitable for medical and diagnostic testing since a label, such as an isotope, may have either radioactive or magnetic properties and thus be easily identified by conventional laboratory testing instruments. In the past, methods directed at producing optically pure D-erythro-sphingomyelins required many steps and resulted in extremely low overall yields. These methods provide very time-consuming and costly means for producing D-erythro-sphingomyelins.

For example, Shapiro et al, *Journal of the American Chemical Society*, 84, 1047 (1962), reported a 14 step procedure commencing from myristaldehyde to D-erythro-sphingomyelin having an overall yield of 0.1%. In another example, Bruzik, *Journal of the Chemical Society, Chemical Communication*, 329 (1986), discloses a 13 step procedure with an undisclosed overall yield. In addition to the undesirable lengthy procedures disclosed by Shapiro et al and Bruzik, both procedures require an additional optical resolution step to separate the resulting diastereomers. This additional separation step increases the number of steps required to produce the desired D-erythro-sphingomyelins. Several other attempts including semi-synthesis approaches have been made at producing sphingomyelins but these attempts have been unsuccessful with regard to the desired high yields and optical purity. A method for producing optically pure sphingomyelins having a high overall yield is extremely desirable in view of the expensive materials required to synthesize sphingomyelins.

Accordingly, there remains a need in the art for a method for making D-erythro-sphingomyelins that results in a high overall yield and permits the introduction of isotopes so as to form an isotopically labeled D-erythro-sphingomyelins useful in conducting scientific studies.

SUMMARY OF THE INVENTION

That need is met by the present invention which provides a method for making an optically pure sphingomyelin, referred to as D-erythro-sphingomyelin. The present method produces D-erythro-sphingomyelin from D-galactose via a protected azide composition. The yield of the present method is much higher than past attempts in the art and thus, is believed to significantly reduce the cost of producing sphingomyelins for scientific studies. While the instant D-erythro-sphingomyelin is originally produced from D-galactose, the present method is particularly directed to a five step procedure beginning with the starting material, a protected azide composition, which may be produced in accordance with known methods.

The present method provides the ability to control the structure of the fatty acid group in the sphingomyelin structure which eliminates the heterogeneity (i.e., mixture) of sphingomyelins from naturally occurring sources. The present method also provides the ability to introduce labels such as, isotopes having radioactive or magnetic properties, at specific sites on the fatty acid group thus rendering the D-erythro-sphingomyelin produced by the present invention particularly useful for identification and testing purposes. The long-chain fatty acid attached to the present sphingomyelin will have an acyl chain containing from about fifteen to twenty-four carbon atoms.

In accordance with one aspect of the present invention, a five step method for making a D-erythro-sphingomyelin composition is provided which includes the steps of: (1) reacting (2S,3R,4E)-2-azido-3-(tert-butyldimethylsilyloxy)-4-octadecen-1-ol, also referred to herein as a protected azide, with triphenylphosphine and water in a solvent to form a (2S,3R,4E)-2-amino-3-(tert-butyldimethylsilyloxy)-4-octadecen-1-ol referred to herein as a protected sphingosine; (2) reacting a long-chain fatty acid with the protected sphingosine in the presence of N-ethoxycarbonyl-2-ethoxy-1,2-dihydroquinoline catalyst, also referred to herein as EEDQ in a second solvent to form (2S,3R,4E)-2-acylamido-3-(tert-butyldimethylsilyloxy)-4-octadecen-1-ol, also referred to herein as a protected ceramide; (3) reacting 2-chloro-2-oxo-1,3,2-dioxaphospholane with the protected ceramide in the presence of triethylamine and 4-dimethylaminopyridine, also referred to herein as DMAP catalyst in a third solvent; to form 2-[(2S,3R,4E)-2-acylamido-3-(tert-butyldimethylsilyloxy)-4-octadecen-1-oxy]-2-oxo-1,3,2-dioxaphospholane, also referred to herein as, protected cyclic phosphotriester; (4) reacting trimethylamine with the protected cyclic phosphotriester in a solvent system to form (2S,3R,4E)-2-acylamido-3-(tert-butyldimethylsilyloxy)-4-octadecen-1-phosphorylcholine, also referred to herein as a protected sphingomyelin; and (5) reacting tetra-n-butylammonium fluoride with said protected sphingomyelin in tetrahydrofuran, also referred to herein as THF; to form D-erythro-sphingomyelin.

The protective functional group in the protected azide reactant used in the present method is a tert-butyldimethylsilyl group. The long-chain fatty acid is preferably selected from the group consisting of palmitic acid, nervonic acid, ligonocenic acid, stearic acid and behenic acid. The labels may be magnetic or isotopic such that they may be easily identified by conventional identification techniques. One or more labels including isotopes, such as $^{13}C$, may be controllably positioned within the fatty acid chain on the D-erythro-sphingomyelin for identification and testing purposes.

Within the five step procedure to which the present invention is directed, the reaction products, protected sphingosine, protected ceramide, protected sphingomyelin and the final product, D-erythro-sphingomyelin, may all be purified by conventional methods such as column chromatography before proceeding with further reaction or use. Since the reaction product, protected cyclic phosphotriester is sensitive to moisture, it should be handled in nitrogen atmosphere and is preferably used immediately in the next reaction step without further purification.

The present invention is also directed to the product produced by the present method. The product, D-erythro-sphingomyelin, is optically pure such that it does not contain any other diastereomers which may inhibit the use of the sphingomyelins in scientific studies. The D-erythro-sphingomyelin product is homogeneous and thus, has the same carbon chain-length within the fatty acid group on each molecule. Conversely, naturally occurring sphingomyelins are heterogeneous having various carbon chain-length fatty acid groups and a multitude of differing backbone long-chain bases even after they are subjected to numerous and extensive separation techniques. Thus, naturally occurring sphingomyelins are not feasible for scientific study.

The D-erythro-sphingomyelin produced in accordance with the present method is especially useful in scientific research, medical studies, diagnostic testing and in the cosmetic industry. Moreover, the present invention provides a labeled D-erythro-sphingomyelin that may be incorporated into biological membranes to study the dynamics of drug delivery across the membranes of blood and nervous systems. The labeled D-erythro-sphingomyelin may be used to study diseases such as atherosclerosis and Niemann-Pick disease.

Accordingly, it is an object of the present invention to provide an improved method for making D-erythrosphingomyelin that has a higher overall yield. It is yet another object of the present invention to provide a method for making a D-erythro-sphingomyelin composition that is homogeneous and optically pure and which may be labeled for identification and testing purposes. These and other objects, features and attendant advantages of the present invention will become apparent to those skilled in the art from a reading of the following detailed description of the preferred embodiment and the appended claims.

DETAILED DESCRIPTION OF THE PREFERRED EMBODIMENT

In the preferred embodiment of the present invention, D-erythro-sphingomyelins are produced by a five step process which converts a reagent derived from D-galactose to the desired D-erythro-sphingomyelin which may be labelled to aid in testing. The preferred method for making D-erythro-sphingomyelin is generally directed to a five step method which uses a protected azide starting material derived from D-galactose to form a protected sphingosine. The protected sphingosine is reacted with a long-chain fatty acid to form a protected ceramide. 2-chloro-2-oxo-1,3,2-dioxaphospholane is then reacted with the protected ceramide to form a protected cyclic phosphotriester. The protected cyclic phosphotriester is thereafter cleaved with trimethylamine to form a protected sphingomyelin. Deprotection of protected sphingomyelin is accomplished by reacting tetra-n-butylammonium fluoride therewith to form the present D-erythro-sphingomyelin composition. The details of the present method are described more fully below.

The backbone of sphingomyelin is sphingosine and thus, sphingosine was first considered as an intermediate in the synthesis of sphingomyelins in this invention. However, it was determined that the conversion of sphingosine to sphingomyelins by way of ceramide is not feasible. The free secondary alcohol group in ceramide precludes the phosphorylation of the primary alcohol group. Thus, instead of sphingosine, a sphingosine analog in which the secondary alcohol group is properly protected would be suitable starting material for the synthesis of sphingomyelins. Of many such sphingosine analogs available in the art, the protected azide (2S,3R,4E)-2-azido-3-tert-butyldimethylsilyloxy)-4-octadecen-1-ol is preferred for the present invention. The protected azide has the following structural formula

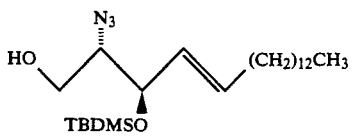

wherein TBDMS is a tert-butyldimethylsilyl group. The protected azide may be produced by the approach disclosed by Zimmermann et al., *Liebigs Ann Chem.*, 663 (1988), the disclosure of which is incorporated herein by reference. A more efficient synthesis is disclosed by Nicolaou et al, *J. Am. Chem. Soc.* 110, 7910, (1988), the disclosure of which is incorporated herein by reference. In the protected azide the secondary alcohol group is protected by tert-butyldimethylsilyl group. This compound is preferred as it can be synthesized in relatively few steps and with relatively high overall yield (5%) from naturally occurring D-galactose. Furthermore, the stereochemistry in it is desirable for D-erythro-sphingomyelins. Most importantly, the tert-butyldimethylsilyl protecting group is stable under the conditions of the synthesis of sphingomyelins and can be conveniently taken off in the final step without influencing the other functional groups in sphingomyelins.

The present invention is most particularly directed to the five step procedure beginning with the starting material, protected azide, which is produced in accordance with the Zimmermann et al procedure. The protected azide starting material, with the invention is reduced with two equivalents of triphenylphosphine in the presence of an excess of water in a solvent. The resulting product is a protected sphingosine having a yield of approximately 91%. The protected sphingosine preferably has the following formula

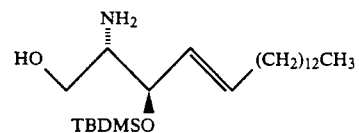

wherein TBDMS is a tert-butyldimethylsilyl group. The solvent used in this step is preferably selected from the group consisting of pyridine, benzene and mixtures thereof.

The second step of the present method is directed to converting the protected sphingosine into an amide by reacting a long-chain fatty acid with the protected sphingosine in the presence of N-ethoxycarbonyl-2-ethoxy-1,2-dihydroquinoline (EEDQ) catalyst in a second solvent thus forming a protected ceramide. The protected ceramide preferably has the formula

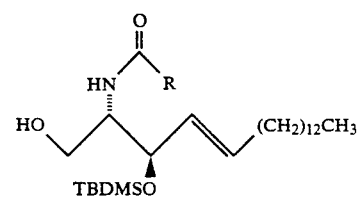

wherein R is an alkyl group from a long-chain fatty acid. The yield of the second step is approximately 92%. The long-chain fatty acid will have an acyl chain including from fifteen to twenty-four carbon atoms. Preferably, the long-chain fatty acid is selected from the group consisting of palmitic acid, nervonic acid, ligonocenic acid, stearic acid and behenic acid. However, it should be understood that any other long-chain fatty acid, including fatty acids with acyl chains having more than twenty-four and less than sixteen carbon atoms, may be substituted therefor. Most preferably, the long-chain fatty acid is palmitic acid so as to produce a N-palmitoyl-D-erythro-sphingomyelin composition. It is also preferable to have the long-chain fatty acid labeled with an isotope.

The isotopes may include any of those known in the art including but not limited to those having radioactive or magnetic properties. The aforementioned isotopes are introduced into the D-erythro-sphingomyelin for the purpose, of providing easy identification with conventional laboratory instruments when conducting scientific studies. The most preferred isotope is $^{13}C$ positioned on the acyl chain of the fatty acid. Such an isotope may be positioned anywhere on the acyl chain. For example, D-erythro-sphingomyelins having $^{13}C$ isotopes located at positions 1, 7 and 12 may be prepared in accordance with the present method. This is accomplished by reacting a $^{13}C$ labeled long-chain fatty acid with the aforementioned protected sphingosine intermediate. Some $^{13}C$ labeled long-chain fatty acids are well known in the art and thus commercially available. For example, palmitic acid having a $^{13}C$ isotope at position 1 on the acyl chain may be purchased from the Sigma Chemical Co. Yet other $^{13}C$ labeled long-chain fatty acids may be produced in accordance with procedures disclosed in the literature. Palmitic acid labeled with $^{13}C$ at position 7 and palmitic acid labeled with $^{13}C$ at position 12 may be produced as described by Uzomba, "Syntheses of Labeled Fatty Acids and Dipalmytoyl-sn-glycerol-3-phosphatidylcholine Dynamic and Order Study of the Acyl Chain Using $^{13}C$ Spin-lattice Relaxation Experiments," *Ph.D. Dissertation*, CA: 112, 77753m may be purchased from Univ. Microfilms Int. Order #DA 8819550 or *Diss. Abstr. Int. B.*, 49(a), 3771-2, (1989) Ohio University (1986), the disclosure of which is incorporated herein by reference.

These isotopically labeled sphingomyelins are particularly useful in scientific studies. One example exhibiting such a use occurs when studying the molecular dynamics and structural organization of lipid bilayers and biological membranes. The $^{13}C$ spin-lattice relaxation is measured to conduct such studies. A D-erythro-sphingomyelin having an isotopically labeled long-chain fatty acid is particularly useful when conducting medical and diagnostic testing. Additionally, various other applications requiring the identification of sphingomyelin in biological processes may conveniently incorporate the use of isotopically labeled, D-erythro-sphingomyelins as produced by the present invention.

The third step of the present method is directed to reacting 2-chloro-2-oxo-1,3,2-dioxaphospholane with the aforementioned protected ceramide in the presence of triethylamine and 4-dimethylaminopyridine (DMAP) catalyst in a third solvent. This reaction step allows for the introduction of the phosphorylcholine moiety, as evidenced by the resulting product which is a protected cyclic phosphotriester. The protected cyclic phosphotriester preferably has the formula

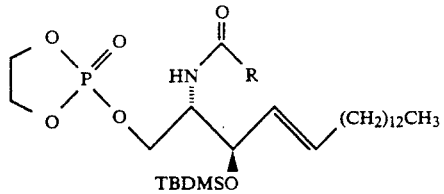

wherein R is an alkyl group from a long-chain fatty acid. The preferable solvent used in this step is benzene. The protected cyclic phosphotriester product is sensitive to moisture and should be handled in nitrogen atmosphere and used very soon after it is produced. Accordingly, the protected cyclic phosphotriester is preferably not purified, but used immediately in the next step of the present method. Unexpectedly, the use of 4-dimethylaminopyridine (DMAP) catalyst increases the yield of the reaction. In the absence of this catalyst,, the yield is substantially less.

The fourth step in producing the desired D-erythro-sphingomyelin is to cleave the cyclic portion of the protected cyclic phosphotriester molecule by reacting it with anhydrous trimethylamine in a solvent system. The product is a protected sphingomyelin preferably having the formula

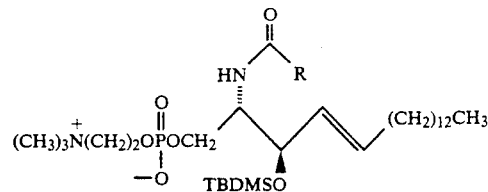

wherein R is an alkyl group from a long-chain fatty acid. The most preferable solvent system comprises benzene and acetonitrile in a 1:1 ratio. It should be appreciated that other compatible solvents or mixtures thereof known in the art may be used in this step which do not adversely affect the yield or the final product produced. The yield calculated from the protected ceramide to the protected sphingomyelin is approximately 56%.

The final step of the present method is directed toward deprotection of the secondary alcohol to thereby form the desired D-erythro-sphingomyelin having the formula

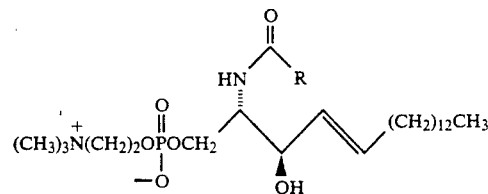

wherein R is an alkyl group from a long-chain fatty acid. Deprotection is accomplished by reacting three equivalents of tetra-n-butylammonium fluoride with the protected sphingomyelin in tetrahydrofuran (THF) solvent. This step is preferably completed at room temperature and results in a yield of 92%. The NMR, IR spectra and Rf value in TLC of the synthesized D-erythro-sphingomyelins are identical to those of the naturally occurring sphingomyelins. The melting point of the present N-palmitoyl D-erythro-sphingomyelin is 213°-215° C. which is consistent with the values reported in the past. For example, Shapiro et al, *Journal of American Chemical Society*, 84, 1047 (1962), reports a N-palmiltoyl D-erythro-sphingomyelin having a melting point of 215°-217° C. The specific rotation, $[\alpha]^{20}_D = +6.8°$, is also consistent with the value $[\alpha]^{25}_D = +6.1$ reported by Shapiro et al in the above publication.

Thus, commencing from the starting material, protected 2-azide-octadecene-1,3-diol, D-erythro-sphingomyelin may be synthesized in accordance with the present method and result in an overall yield of 43%. The overall yield from D-galactose to D-erythro-sphingomyelin is approximately 2.2% and as stated previously, past attempts in the art report yields that are much lower. For example, Shapiro reports a yield of 0.1% from myristaldehyde to sphingomyelin. Accordingly, the present method provides an improvement of at least twenty-fold over past attempts at producing homogeneous sphingomyelins. Moreover, the resulting D-erythro-sphingomyelin is optically pure and does not contain any diastereomers which may inhibit subsequent use of the sphingomyelins in scientific studies. The present method permits the introduction of labels onto the sphingomyelin molecule and as mentioned, this feature is particularly useful in medical and diagnostic testing.

The present method is also advantageous from the standpoint of the timing of the introduction of the long-chain fatty acid moiety in the synthesis. More particularly, the long-chain fatty acid is introduced only four steps before the final product, D-erythro-sphingomyelin, thus making the present method suitable for the syntheses of a series of optically pure sphingomyelins having different acyl groups attached thereto. For example, a large amount of starting material, protected azide, may be produced in accordance with Zimmermann et al and thereafter, the present five step method may be followed to produce various final products each being a D-erythro-sphingomyelin composition having a different acyl group attached thereto. Each sphingomyelin may then be used in a variety of scientific studies. Accordingly, the versatility of the present method in producing a multitude of labeled D-erythro-sphingomyelins is exhibited.

In order to make the present invention more readily understood, reference is made to the following examples, which are intended to be illustrative of the invention, but are not intended to be limiting in scope.

EXAMPLE 1

Synthesis of D-erythro-Sphingomyelin

The starting material, protected azide, was prepared according to the procedure described by Zimmermann et al. In particular, 2.73 grams (6.21 mmol) of starting material was produced. The five step procedure to which the present invention is particularly directed was then followed.

STEP 1

A solution containing 600 mg (1.36 mmol) of protected azide ((2S,3R,4E)-2-azido-3-(tert-butyldimethylsilyloxy)-4-octadecen-1-ol), triphenylphosphine (720 mg, 2.75 mmol), and water (740 mg, 41.0 mmol) in pyridine (35 mL) was stirred at 55°–60° C. for 11 hours. The solvent was removed, under reduced pressure, and the residue was purified by column chromatography on silica gel, eluting with a) $CH_2Cl_2$/MeOH (97.5:2.5) and b) $CH_2Cl_2$(MeOH (95:5). 510 mg of the pure product, protected sphingosine ((2S,3R,4E)-2-amino-3-(tert-butyldimethylsilyloxy)-4-octadecen-1-ol), was obtained as a colorless oil. The yield of this step was 91%.

STEP 2

A solution of protected sphingosine ((2S,3R,4E)-2-amino-3-(tert-butyldimethylsilyloxy)-4-octadecen-1-ol) (250 mg, 0.604 mmol), palmitic acid (217 mg, 0.846 mmol), and EEDQ (299 mg, 1.21 mmol) in dry ethanol (40 mL) was stirred at 50° C. for 14 hours. The solvent was removed under reduced pressure, and the residue was purified by using a Chromatotron: silica gel plate, eluting with petroleum ether/ethyl acetate (9:1). 361 mg of the product, protected ceramide ((2S,3R,4E)-2-hexadecanoylamido-3-(tert-butyldimethylsilyloxy)-4-octadecen-1-ol), was obtained as a white solid. The yield of this step was 92%.

STEP 3

A solution of protected ceramide ((2S,3R,4E)-2-hexadecanoylamido-3-(tert-butyldimethylsilyloxy)-4-octadecen-1-ol) (224 mg, 0.343 mmol), triethylamine (59.0 mg, 0.583 mmol), and a catalytic amount of DMAP (about 2 mg) in dry benzene (3 mL) was cooled down to +8° C. To this was added dropwise 2-chloro-2-oxo-1,3,2-dioxaphospholane (68.4 mg in 1 mL dry benzene, 0.480 mmol). The mixture was then warmed to room temperature and stirred for 6 hours. After the crystalline triethylamine hydrochloride was removed by filtration, the solvent was evaporated under reduced pressure. The product, protected cyclic phosphotriester, 2-[(2S,3R,4E)-2-hexadecanoylamido-3-(tert-butyldimethylsilyloxy)-4-octadecen-1-oxy]-2-oxo-1,3,2,-dioxaphospholane was obtained as a white solid residue.

STEP 4

All of the product obtained in Step 3 was dissolved in 3 mL of a mixed solvent $C_6H_6$/MeCN 1:1) system and transferred into a pressure bottle. The solution was cooled down to −78° C. and an excess (about 1 mL) of anhydrous trimethylamine was allowed to condense into the solution. The bottle was sealed and the solution was heated at 65°–70° C. for 48 hours. Then, it was cooled down to room temperature and the solvents were removed under reduced pressure. The residue was purified by column chromatography on silica gel, eluting with $CHCl_3$/MeOH/$H_2O$ (65:25:4). 156 mg of the pure product, protected sphingomyelin, (2S,3R,4E)-2-hexadecanoylamido-3-(tert-butyldimethylsilyloxy)-4-octadecen-1-phosphorylcholine was obtained as a white solid. The yield of the above two steps from protected ceramide to protected sphingomyelin was 56%.

STEP 5

To a solution of the protected sphingomyelin (2S,3R,4E)-2-hexadecanoylamido-3-(tert-butyldimethylsilyloxy)-4-octadecen-1-phosphorylcholine (105 mg, 0.128 mmol) in dry THF (6 mL) was added dropwise tetra-n-butylammonium fluoride (0.384 mL @ 1M in THF, 0.384 mmol) at 0° C. The mixture was warmed to room temperature and stirred for 20 hours. Several drops of water were added to quench the reaction. The solvent was removed under reduced pressure, and the residue was purified by a) column chromatography on silica gel, eluting with $CHCl_3$/MeOH/$H_2O$ (65:25:4); b) ion exchange chromatography on a mixed bed of Amberlite CG-50/Amberlite IRA-45 (1:1), eluting with $CHCl_3$/MeOH/$H_2O$ (65:25:4); and c) recrystallization from acetone with a small portion of $CHCl_3$/MeOH (1:1) in it. 83 mg of the pure N-palmitoyl-D-erythro-sphingomyelin (83 mg, 92%) was obtained as a white solid. The yield of this step was 92%.

The overall yield from the starting material, protected azide to the final product, N-palmitoyl-D-erythro-sphingomyelin, was 43%. The overall yield from D-galactose to N-palmitoyl-D-erythro-sphingomyelin was 2.2%.

EXAMPLE 2

Synthesis of Isotopically Labeled D-erythro-Sphingomyelin

N-Palmitoyl-D-erythro-Sphingomyelin labeled with $^{13}C$ at position 1 on the palmitoyl chain Step 1 was followed as described in Example 1 to obtain protected sphingosine product. Protected sphingosine (168 mg, 0.407 mmol), palmitic acid labeled with $^{13}C$ at position 1 (147 mg, 0.570 mmol), purchased from Sigma Chemical Co. (product #29,212-5), was reacted as described above in Step 2 to yield 244 mg (0.374 mmol) of the product, $^{13}C$ labeled protected ceramide. The yield of this step was 92%.

Steps 3 and 4 were followed as described in Example 1 using $^{13}C$ labeled protected ceramide (215 mg, 0.329 mmol) to yield 151 mg (0.186 mmol) of $^{13}C$ labeled protected sphingomyelin. The yield of these steps was 56%.

Step 5 was followed as described in Example 1 using $^{13}C$ labeled protected sphingomyelin (90 mg, 0.11 mmol) to yield 71 mg (0.10 mmol) of N-palmitoyl-D-erythro-sphingomyelin labeled with $^{13}C$ at position 1 in the palmitoyl chain. The yield of this step was 92%.

EXAMPLE 3

Synthesis of Isotopically Labeled D-erythro-Sphingomyelin

N-Palmitoyl-D-erythro-Sphingomyelin labeled with $^{13}C$ at position 7 on the palmitoyl chain Step 1 was followed as described in Example 1 to obtain protected sphingosine product. Protected sphingosine (71 mg, 0.172 mmol) and palmitic acid labeled with $^{13}C$ at position 7 (62 mg, 0.241 mmol) made in accordance with the procedure disclosed in Uzomba, as referenced above, was reacted as described above in Step 2 to yield 102 mg (0.156 mmol) of the product, $^{13}C$ labeled protected ceramide. The yield of this step was 91%.

Steps 3 and 4 were followed as described in Example 1 using $^{13}C$ labeled protected ceramide (102 mg, 0.156 mmol) to yield 70 mg (0.086 mmol) of $^{13}C$ labeled protected sphingomyelin. The yield of these steps was 55%.

Step 5 was followed as described in Example 1 using $^{13}C$ labeled protected sphingomyelin (70 mg, 0.086 mmol) to yield 56 mg (0.080 mmol) of N-palmitoyl-D-erythro-sphingomyelin labeled with $^{13}C$ at position 7 in the palmitoyl chain. The yield of this step was 93%.

EXAMPLE 4

Synthesis of Isotopically Labeled D-erythro-Sphingomyelin

N-Palmitoyl-D-erythro-Sphingomyelin labeled with $^{13}C$ at position 12 on the palmitoyl chain Step 1 was followed as described in Example 1 to obtain protected sphingosine product. Protected sphingosine (93 mg, 0.225 mmol) and palmitic acid labeled with $^{13}C$ at position 12 (81 mg, 0.315 mmol) Uzomba, as referenced above, was reacted as described above in Step 2 to yield 135 mg (0.207 mmol) of the product, $^{13}C$ labeled protected ceramide. The yield of this step was 92%.

Steps 3 and 4 were followed as described in Example 1 using $^{13}C$ labeled protected ceramide (135 mg, 0.207 mmol) to yield 95 mg (0.116 mmol) of $^{13}C$ labeled protected sphingomyelin. The yield of these steps was 56%.

Step 5 was followed as described in Example 1 using $^{13}C$ labeled protected sphingomyelin (65 mg, 0.079 mmol) to yield 51 mg (0.072 mmol) of N-palmitoyl-D-erythro-sphingomyelin labeled with $^{13}C$ at position 12 in the palmitoyl chain. The yield of this step was 91%.

Having thus described the invention in detail, it will be obvious to those skilled in the art that various changes may be made without departing from the scope of the invention and the invention is not to be considered limited to what is described in the specification.

What is claimed is:

1. A method for making a D-erythro-sphingomyelin composition comprising the steps of:
   (a) reacting a (2S,3R,4E)-2-azido-octadecen-1,3-diol composition having a protective functional group attached to the secondary alcohol group thereof with a solution of triphenylphosphine and water in a first solvent to form a protected sphingosine;
   (b) reacting a long-chain fatty acid with said protected sphingosine in the presence of N-ethoxycarbonyl-2-ethoxy-1,2-dihydroquinoline catalyst in a second solvent to form a protected ceramide;
   (c) reacting 2-chloro-2-oxo-1,3,2-dioxaphospholane with said protected ceramide in the presence of triethylamine and 4-dimethylaminopyridine catalyst in a third solvent to form a protected cyclic phosphotriester;
   (d) reacting trimethylamine with said protected cyclic phosphotriester in a solvent system to form a protected sphingomyelin; and
   (e) reacting tetra-n-butylammonium, fluoride with said protected sphingomyelin in tetrahydrofuran to form said D-erythro-sphingomyelin composition.

2. The method of claim 1 wherein said protective functional group is selected from the group consisting of tert-butyldimethylsilyl and tert-butyldiphenylsilyl groups.

3. The method of claim 1 wherein said first solvent is selected from the group consisting of pyridine, benzene and mixtures thereof.

4. The method of claim 1 wherein said second solvent is ethanol, and said third solvent is benzene.

5. The method of claim 1 wherein said solvent system comprises benzene and acetonitrile in a 1:1 ratio.

6. The method of claim 1 wherein said protected azide has the formula

wherein TBDMS is a tert-butyldimethylsilyl group.

7. The method of claim 1 wherein said protected sphingosine has the formula

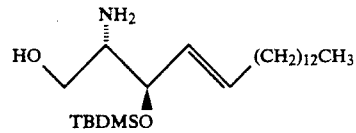

wherein TBDMS is a tert-butyldimethylsilyl group.

8. The method of claim 1 wherein said long-chain fatty acid has an acyl group with at least 15 carbon atoms.

9. The method of claim 1 wherein said long-chain fatty acid is selected from the group consisting of palmitic acid, nervonic acid, ligonocenic acid, stearic acid and behenic acid.

10. The method of claim 1 wherein said fatty acid is palmitic acid.

11. The method of claim 1 wherein said fatty acid is labeled with an isotope positioned on the acyl chain of said fatty acid.

12. The method of claim 11 wherein said isotope is $^{13}C$ located at position 12 on the acyl chain of said long-chain fatty acid.

13. The method of claim 1 wherein said protected ceramide has the formula

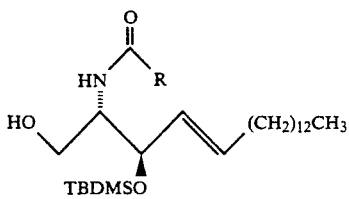

wherein R is an alkyl group formed from said fatty acid and TBDMS is a tert-butyldimethylsilyl group.

14. The method of claim 1 wherein said protected cyclic phosphotriester has the following formula

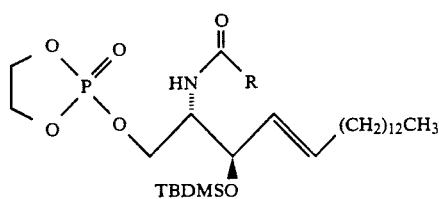

wherein R is an alkyl group formed from said fatty acid and TMDMS is a tert-butyldimethylsilyl group.

15. The method of claim 1 wherein said protected sphingomyelin has the formula

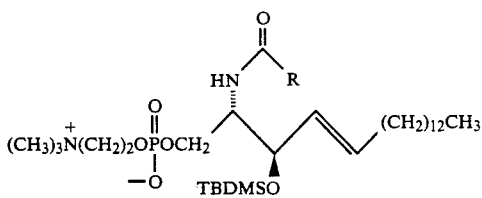

wherein R is an alkyl group formed from said fatty acid and TBDMS is a tert-butyldimethylsilyl group.

16. The method of claim 1 wherein said D-erythro-sphingomyelin has the formula

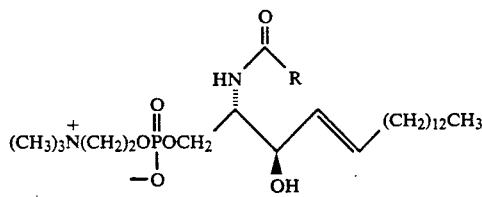

wherein R is an alkyl group derived from said fatty acid.

17. The method of claim 1 wherein the ratio of said triphenylphosphine to said protected azide is 2:1.

18. The method of claim 1 wherein the ratio of said tetra-n-butylammonium fluoride to said protected sphingomyelin is 3:1.

19. A method for making a D-erythro-sphingomyelin composition comprising the steps of:
  (a) reacting a (2S,3R,4E)-2-azido-octadecen-1,3-diol composition having a protective functional group attached to the secondary alcohol group thereof with a solution of triphenylphosphine and water in a first solvent to form a protected sphingosine; purifying said protected sphingosine by column chromatography;
  (b) reacting a long-chain fatty acid with said protected sphingosine in the presence of N-ethoxycarbonyl-2-ethoxy-1,2-dihydroquinoline catalyst in a second solvent to form a protected ceramide; purifying said protected ceramide by column chromatography;
  (c) reacting 2-chloro-2-oxo-1,3,2-dioxaphospholane with said protected ceramide in the presence of triethylamine and 4-dimethylaminopyridine catalyst in a third solvent to form a protected cyclic phosphotriester;
  (d) reacting trimethylamine with said protected cyclic phosphotriester in a solvent system to form a protected sphingomyelin; purifying said protected sphingomyelin by column chromatography; and
  (e) reacting tetra-n-butylammonium fluoride with said protected sphingomyelin in tetrahydrofuran to form said D-erythro-sphingomyelin composition; purifying said D-erythro-sphingomyelin by chromatography and recrystallization.

20. A method for making a D-erythro-sphingomyelin composition comprising the steps of:
  (a) reacting a (2S,3R,4E)-2-azido-octadecen-1,3-diol composition having a protective functional group attached to the secondary alcohol group thereof with a solution of triphenylphosphine and water in a first solvent;
  (b) reacting a long-chain fatty acid with said protected sphingosine in the presence of N-ethoxycarbonyl-2-ethoxy-1,2-dihydroquinoline catalyst in a second solvent; agitating said protected sphingosine and said long-chain fatty acid for at least 14 hours to form a protected ceramide;
  (c) reacting 2-chloro-2-oxo-1,3,2-dioxaphospholane with said protected ceramide in the presence of triethylamine and 4-dimethylaminopyridine catalyst in a third solvent; agitating and heating said protected ceramide, said triethylamine and said 2-chloro-2-oxo-1,3,2-dioxaphospholane to form a protected cyclic phosphotriester;
  (d) reacting trimethylamine with said protected cyclic phosphotriester in a solvent system; heating said protected cyclic phosphotriester and said trimethylamine for at least 48 hours to form a protected sphingomyelin; and
  (e) reacting tetra-n-butylammonium fluoride with said protected sphingomyelin in tetrahydrofuran; agitating and heating said protected sphingomyelin and said tetra-n-butylammonium fluoride for at least 20 hours to form said D-erythro-sphingomyelin composition.

* * * * *